United States Patent [19]
Ward et al.

[11] Patent Number: 5,013,837
[45] Date of Patent: May 7, 1991

[54] 3-ARYLCARBONYL-1H-INDOLE-CONTAINING COMPOUNDS

[75] Inventors: Susan J. Ward; Malcolm R. Bell, both of East Greenbush, N.Y.

[73] Assignee: Sterling Drug Inc., New York, N.Y.

[21] Appl. No.: 562,366

[22] Filed: Aug. 3, 1990

Related U.S. Application Data

[62] Division of Ser. No. 490,201, Mar. 8, 1990.

[51] Int. Cl.$^5$ .................. C07D 413/06; C07D 413/14
[52] U.S. Cl. ..................................... 544/143; 544/139
[58] Field of Search ............................... 544/139, 142

[56] References Cited

U.S. PATENT DOCUMENTS

| | | | |
|---|---|---|---|
| 3,489,770 | 1/1970 | Herbst | 544/143 |
| 3,946,029 | 3/1976 | Deschamps et al. | 544/131 |
| 4,581,354 | 10/1988 | Bell | 514/210 |

Primary Examiner—Robert W. Ramsuer
Attorney, Agent, or Firm—William G. Webb; Paul E. Dupont

[57] ABSTRACT

Antiglaucoma compositions containing 3-aryl-carbonyl-1-aminoalkyl-1H-indoles, as the active component thereof, and a method of use thereof in the treatment of glaucoma.

11 Claims, No Drawings

3-ARYLCARBONYL-1H-INDOLE-CONTAINING COMPOUNDS

This application is a division of application Ser. No. 490,201, filed Mar. 8, 1990.

BACKGROUND OF THE INVENTION (a) Field of the Invention

This invention relates to 2-$R_2$-3-arylcarbonyl-1-aminoalkyl-1H-indole-containing antiglaucoma compositions and method of use thereof.

(b) Information Disclosure Statement

Deschamps et al. U.S. Pat. No. 3,946,029 discloses compounds having the formula:

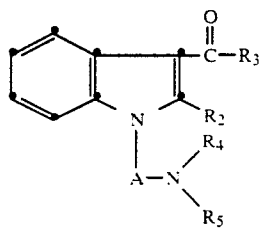

where A is alkylene; $R_2$ is one to four carbon alkyl, phenyl or phenyl substituted by fluorine, chlorine, bromine, methoxy or cyclohexyl; $R_3$ is a 2-, 3- or 4-pyridyl group; and $R_4$ and $R_5$ are either the same or different 1-5 carbon alkyl or $R_4$ and $R_5$ are joined together to form, with the nitrogen atom, a piperidino, pyrrolidino or morpholino group. The compounds are said to possess fibrinolytic and anti-inflammatory activities.

Essentially the same disclosure is found in Inion et al., Eur. J. of Med. Chem., 10 (3), 276-285 (1975). Specifically disclosed in both these references is the species, 2-isopropyl-3-(3-pyridylcarbonyl)-1-[2-(4-morpholinyl)ethyl]-indole.

Herbst U.S. Pat. No. 3,489,770 generically discloses compounds having the formula:

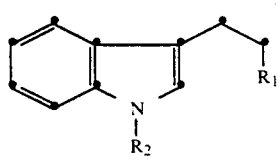

where $R_1$ is "diloweralkylamino, pyrrolidinyl, piperidino and morpholino and $R_2$ is selected from the group consisting of cyclo(lower)alkanoyl and adamantanyl-carbonyl". Although not within the ambit of the above-defined genus, the Herbst patent also discloses a variety of species where $R_2$ is an arylcarbonyl group. The compounds are said to possess anti-inflammatory, hypotensive, hypoglycemic and CNS activities.

Tambute, Acad. Sci. Comp. Rend., Ser. C, 278 (20), 1239-1242 (1974) discloses compounds of the formula:

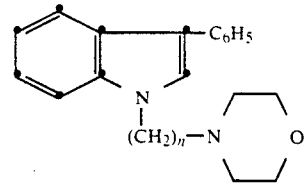

where n is 2 or 3. No utility for the compounds is given.

Bell U.S. Pat. No. 4,581,354 discloses 3-arylcarbonyl- and 3-cycloalkylcarbonyl-1-aminoalkyl-1H-indoles which are useful as analgesic, antirheumatic and anti-inflammatory agents.

SUMMARY

In a composition aspect, the invention relates to compositions for the treatment of glaucoma which comprises a pharmaceutical carrier and an effective intraocular pressure reducing amount of a 2-$R_2$-3-$R_3$-carbonyl-1-aminoalkyl-1H-indole or a pharmaceutically acceptable acid-addition salt thereof.

In a method aspect, the invention relates to a method for the treatment of glaucoma which comprises administering to a patient in need of such treatment a medicament containing an effective intraocular pressure reducing amount of a 2-$R_2$-3-$R_3$-carbonyl-1-aminoalkyl-1H-indole or a pharmaceutically acceptable acid-addition salt thereof.

In a composition of matter aspect, the invention relates to certain novel 2-$R_2$-3-$R_3$-carbonyl-1H-indoles which are useful as antiglaucoma agents.

DETAILED DESCRIPTION OF THE PREFERRED EMBODIMENTS

More specifically, the invention relates to antiglaucoma compositions containing, as the active ingredient thereof, a 2-$R_2$-3-$R_3$-carbonyl-1-aminoalkyl-1H-indole having the formula:

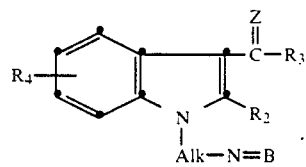

where:

$R_2$ is hydrogen, lower-alkyl, chloro or fluoro;

$R_3$ is phenyl (or phenyl substituted by from one to three substitutents selected from halo, lower-alkoxy, lower-alkoxymethyl, hydroxy, lower-alkyl, amino, lower-alkylamino, di-lower-alkylamino or lower-alkylmercapto), methylenedioxyphenyl, benzyl, styryl, lower-alkoxystyryl, 1- or 2-naphthyl (or 1- or 2-naphthyl substituted by from one to two substituents selected from loweralkyl, lower-alkoxy, halo or cyano), (1H-imidazol-1-yl)naphthyl, 2-(1-naphthyl)ethenyl, 1-(1,2,3,4-tetrahydronaphthyl), anthryl, phenanthryl, pyrenyl, 2-, 3-, 4-, 5-, 6- or 7-benzo[b]furyl, 2- or 3-benzo[b]thienyl, 5-(1H-benzimidazolyl) or 2-, 3-, 4-, 5-, 6-, 7- or 8-quinolyl;

$R_4$ is hydrogen or lower-alkyl, hydroxy, lower-alkoxy or halo in the 4-, 5-, 6- or 7-positions;

Z is O or S;

Alk is lower-alkylene having the formula $(CH_2)_n$ where n is the integer 2 or 3, or such lower-alkylene substituted by a lower-alkyl group; and N=B is N,N-di-lower-alkylamino, 4-morpholinyl, 2-lower-alkyl-4-morpholinyl, 3-lower-alkylmorpholinyl, 1-(pyrrolidinyl, 1-piperidinyl or 3-hydroxy-1-piperidinyl.

Also within the ambit of the invention are certain novel compounds of formula I above where:

$R_2$ is hydrogen or lower-alkyl;

$R_3$ is lower-alkoxymethylphenyl, tri-lower-alkoxyphenyl, benzyl, lower-alkoxystyryl, (1H-imidazol-1-yl)-naphthyl, 2-(1-naphthyl)ethenyl, 1-(1,2,3,4-tetrahydronaphthyl), anthryl, phenanthryl or pyrenyl;

$R_4$ is hydrogen;

Z is O;

Alk is 1,2-ethylene; and

N=B is 4-morpholinyl.

As used herein, unless specifically defined otherwise, the terms lower-alkyl and lower-alkoxy mean monovalent, aliphatic radicals, including branched chain radicals, of from one to about four carbon atoms, for example, methyl, ethyl, propyl, isopropyl, butyl, sec.-butyl, methoxy, ethoxy, propoxy, isopropoxy, butoxy and sec.-butoxy.

As used herein, the term halo means fluoro, chloro or bromo.

The compounds of formula I are prepared by the methods described in detail in Bell U.S. Pat. No. 4,581,354, the disclosure of which is incorporated herein by reference, and many of the compounds of formula I, as well as intermediates used in their preparation, are specifically disclosed therein.

In one method disclosed in the Bell patent, the compounds of formula I where Z is O are prepared by reacting a 2-$R_2$-$R_4$-substituted-3-$R_3$-carbonyl-1H-indole with an amino-lower-alkyl halide or an amino-lower-alkyl tosylate, X-Alk-N=B, in the presence of an acid-acceptor, where X is a halogen atom or a toluenesulfonyloxy group and Alk and N=B have the meanings given above. The reaction is preferably carried out in an organic solvent inert under the conditions of the reaction, such as dimethylformamide (hereinafter DMF), dimethylsulfoxide (hereinafter DMSO), a lower-alkanol or acetonitrile. Suitable acid-acceptors are an alkali metal carbonate, such as sodium carbonate or potassium carbonate, or an alkali metal hydride, such as sodium hydride, an alkali metal amide, such as sodamide, or an alkali metal hydroxide, such as potassium hydroxide. Preferred solvents are DMF and DMSO, and preferred acid-acceptors are sodium hydride, potassium carbonate and potassium hydroxide. The reaction is carried out at a temperature in the range from around 0° C. to the boiling point of the solvent used.

The 2-$R_2$-$R_4$-substituted-3-$R_3$-carbonyl-1H-indoles are in turn prepared by reacting a 2-$R_2$-$R_4$-substituted-indole with a lower-alkyl magnesium halide and reacting the resulting Grignard with an appropriate $R_3$-carboxylic acid halide. The reaction is carried out in an organic solvent inert under the conditions of the reaction, such as dimethyl ether, dioxane or tetrahydrofuran (hereinafter THF), at a temperature in the range from −5° C. to the boiling point of the solvent used.

In another method, the compounds of formula I where Z is O are prepared by reacting a 2-$R_2$-$R_4$-substituted-1-aminoalkyl-1H-indole with an appropriate $R_3$-carboxylic acid halide ($R_3$—CO—X) in the presence of a Lewis acid, such as aluminum chloride, and in an organic solvent inert under the conditions of the reaction. Suitable solvents are chlorinated hydrocarbons such as methylene dichloride (hereinafter MDC) or ethylene dichloride (hereinafter EDC). The reaction is carried out at a temperature from 0° C. to the boiling point of the solvent used.

The intermediate 2-$R_2$-$R_4$-substituted-1-aminoalkyl-1H-indoles are prepared by one of two methods. In one method, a 2-$R_2$-$R_4$-substituted-indole is reacted with an amino-lower-alkyl halide or an amino-lower-alkyl tosylate, X-Alk-N=B, where X, Alk and N=B have the meanings given above, in the presence of an acid-acceptor, in an organic solvent inert under the conditions of the reaction using the same conditions described above for the preparation of the compounds of formula I by alkylation of a 2-$R_2$-$R_4$-substituted-indole with an amino-alkyl halide or tosylate.

In a second method, a 2-$R_2$-$R_4$-substituted-indole is reacted with a halo-lower-alkanamide, X-Alk'CO-N=B, where Alk' is lower-alkylene, $(CH_2)_{n'}$, where n' is the integer 1 or 2, or such lower-alkylene substituted by a lower-alkyl group, and X and N=B have the meanings given above. The reaction is carried out in the presence of a strong base, and the resulting 2-$R_2$-$R_4$-substituted-1H-indole-1-alkanamide is then reduced with lithium aluminum hydride. The reaction of the 2-$R_2$-$R_4$-substituted-indole with the halo-lower-alkanamide is carried out in an appropriate organic solvent, such as DMF, at a temperature from −5° C. to about 50° C. The reduction of the amides with lithium aluminum hydride is carried out in an inert organic solvent, such as diethyl ether, THF or dioxane, at a temperature from −5° C. to about 50° C.

In another method for preparing the compounds of formula I where Z is O, a 2-$R_2$-$R_4$-substituted-3-$R_3$-carbonyl-1-(tosyloxy-lower-alkyl)- or 1-(halo-lower-alkyl)-1H-indole is reacted with a molar equivalent amount of an amine, H-N=B, in an organic solvent inert under the conditions of the reaction, such as acetonitrile, a lower-alkanol or DMF. The reaction is preferably carried out by heating a solution of the reactants at the boiling point of the mixture.

The 2-$R_2$-$R_4$-substituted-3-$R_3$-carbonyl-1-(2-tosyloxyethyl)- or 1-(2-haloethyl)-1H-indoles, where Alk is 1,2-ethylene, are in turn prepared by reaction of a 2-$R_2$-$R_4$-substituted-3-$R_3$-carbonyl indole with a lower-alkyl lithium, for example n-butyl lithium, in an inert organic solvent, such as THF, dioxane or diethyl ether, followed by reaction of the resulting lithium salt with ethylene oxide. Reaction of the resulting 2-$R_2$-$R_4$-substituted-3-$R_3$-carbonyl-1-(2-hydroxyethyl)-1H-indole with toluenesulfonyl chloride in the presence of an acid-acceptor affords the 1-(2-tosyloxyethyl)-1H-indoles, while reaction of the product with a phosphorus trihalide affords the corresponding 1-(2-haloethyl)-1H-indoles.

The 2-$R_2$-$R_4$-substituted-3-$R_3$-carbonyl-1-(halolower-alkyl)-1H-indoles, where Alk has the other possible meanings, are prepared by reaction of a 2-$R_2$-$R_4$-substituted-3-$R_3$-carbonyl indole with a dihalo-lower-alkane in the presence of a strong base, such as sodium hydride in an inert organic solvent, such as DMF. The reaction generally occurs at ambient temperature.

The compounds of formula I where Z is S are prepared by heating the corresponding compounds where Z is O with phosphorus pentasulfide in pyridine.

By further chemical manipulations of various functional groups in the compounds prepared by one or more of the above-described methods, other compounds within the ambit of formula I can be prepared. For example the compounds where $R_3$ is aminophenyl are advantageously prepared from the corresponding species where $R_3$ is nitrophenyl by reduction of the latter.

The reduction can be carried out either catalytically with hydrogen, for example over a platinum oxide catalyst at ambient temperature and in an appropriate organic solvent, such as a lower-alkanol, ethyl acetate or acetic acid or mixtures thereof, and at hydrogen pressures from around 30 to 60 p.s.i.g. Alternatively the reduction can be carried out chemically, for example with iron in the presence of hydrochloric acid in an appropriate organic solvent, for example a lower-alkanol. The reaction is carried out at temperatures from ambient to the boiling point of the solvent used for the reaction.

Other simple chemical transformations which are entirely conventional and well known to those skilled in the art of chemistry and which can be used for effecting changes in functional groups attached to the $R_3$-carbonyl group, $(C=O)R_3$, involve cleavage of aryl ether functions, for example with a pyridine hydrohalide salt to produce the corresponding phenolic compound ($R_3$ is hydroxyphenyl); preparation of compounds where $R_3$ is phenyl or naphthyl substituted by an amine or cyano function by reaction of the corresponding halophenyl or halonaphthyl species with an appropriate amine in the presence of a cuprous halide or with cuprous cyanide, respectively; catalytic debenzylation of benzyloxy-substituted species to prepare the corresponding phenolic compound ($R_3$ is hydroxyphenyl); or reductive alkylation of amino-substituted species to prepare the corresponding di-lower-alkylamino substituted species.

The compounds of formula I in free base form are converted to the acid-addition salt form by interaction of the base with an acid. In like manner, the free base can be regenerated from the acid-addition salt form in conventional manner, that is by treating the salts with cold, weak aqueous bases, for example alkali metal carbonates and alkali metal bicarbonates. The bases thus regenerated can be interacted with the same or a different acid to give back the same or a different acid-addition salt. Thus the bases and all of their acid-addition salts are readily interconvertible.

It will thus be appreciated that formula I not only represents the structural configuration of the bases of formula I but is also representative of the structural entities which are common to all of the compounds of formula I whether in the form of the free base or in the form of the acid-addition salts of the base. It has been found that, by virtue of these common structural entities, the bases of formula I and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically acceptable acids, that is acids whose anions are innocuous to the animal organism in effective doses of the salts so that beneficial properties inherent in the common structural entity represented by the free bases are not vitiated by side effects ascribable to the anions.

In utilizing this pharmacological activity of the salts of formula I, it is preferred, of course, to use pharmaceutically acceptable salts. Although water insolubility, high toxicity or lack of crystalline character may make some particular salt species unsuitable or less desirable for use as such in a given pharmaceutical application, the water-insoluble or toxic salts can be converted to the corresponding pharmaceutically acceptable bases by decomposition of the salts with aqueous base as explained above, or alternatively they can be converted to any desired pharmaceutically acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically acceptable free bases by reaction of the salts with aqueous base, or alternatively they can be converted to a pharmaceutically acceptable acid-addition salt by, for example, ion-exchange procedures.

The acid-addition salts are prepared by reacting the free base and the acid in an organic solvent and isolating the salt directly or by concentration of the solution.

In standard pharmacological test procedures, the compounds of formula I have been found to possess cannabinoid receptor agonist activity and are thus indicated to be useful as anti-glaucoma agents.

It has been shown previously that smoking marijuana reduces intraocular pressure in man [Helper and Frank, Marijuana Smoking and Intraocular Pressure., J. Am. Med. Assoc. 217, 1392 (1971)]. Topical application or systemic injection of delta-9 tetrahydrocannabinol, a principal active ingredient in marijuana, also reduces intraocular pressure [Purnell and Gregg, delta-9 Tetrahydrocannabinol, Euphoria and Intraocular Pressure in Man., Ann. Opth. 7, 921–923 (1975); Green and Pederson, Effect of delta-9 Tetrahydrocannabinol on Aqueous Dynamics and Ciliary Body Permeability in the Rabbit Eye., Exptl. Eye Research 15, 499–507 (1973); Colasanti, Craig and Allara, Intraocular Pressure, Ocular Toxicity and Neurotoxicity after Administration of Cannabinol or Cannibigerol, Exptl. Eye Research 39, 252–259 (1984)]. Similarly, synthetic cannabinoids also reduce intraocular pressure [Green, Symunds, Oliver and Elijah, Intraocular Pressure Following Systemic Administration of Cannabinoids, Curr Eye Research 2, 247–253 (1982); Tiedeman, Shields, Weber, Crow, Coccetto, Harris and Howes, Ophthalmology, 88, 270–277 (1981); Colasanti et al., supra]. Cannabinoid receptor binding sites can be defined as those to which radiolabelled 4-(1,1-dimethylheptyl)-2,3'-dihydroxy-6'alpha-(3-hydroxypropyl)-1',2',3',4',5',6'-hexahydrobiphenyl (CP 55940) binds in a specific and saturable manner, and the binding sites are heterogeneously distributed in the brain [Devane, Dysarz, Johnson, Melvin and Howlett, Determination and Characterization of a Cannabinoid Receptor in Rat Brain, Molecular Pharm. 34, 605–613 (1988)]. Natural and synthetic cannabinoids and representative examples of the compounds of the present invention bind to CP 55940 binding sites. Classification of whether a molecule is an agonist or an antagonist can be made using a mouse vasa deferentia (MVD) preparation in vitro, compounds which inhibit contractions in the MVD preparation being considered active as agonists and those which do not inhibit contractions being considered antagonists. It is believed that agonist activity at the cannabinoid receptor mediates the antiglaucoma actions of cannabinoids, and that agonist activity at this receptor correlates with ocular pressure lowering actions in man. Accordingly the cannabinoid receptor agonist activity of the compounds of formula I indicate their usefulness in reducing ocular pressure and hence in treating glaucoma.

The compounds of formula I can be prepared for pharmaceutical use by incorporating them in unit dosage form as tablets or capsules for oral administration either alone or in combination with suitable adjuvants such as calcium carbonate, starch, lactose, talc, magnesium stearate, gum acacia and the like. Still further, the compounds can be formulated for oral or topical administration either in aqueous solutions of the water soluble salts or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus be determined by the clinician after a consideration of all criteria and using his best judgment on the patient's behalf.

The molecular structures of the compounds of formula I were assigned on the basis of study of their infrared, ultraviolet and NMR spectra. The structures were confirmed by the correspondence between calculated and found values for elementary analyses for the elements.

The following examples will further illustrate the invention without, however, limiting it thereto. All melting points are uncorrected.

PREPARATION OF INTERMEDIATES

A. The 2-$R_2$-$R_4$-Substituted-3-$R_3$-carbonyl indoles

Preparation 1A

To a solution of 0.05 mole of methyl magnesium bromide in about 45 ml. of anhydrous diethyl ether at 0° C. under a nitrogen atmosphere was added, dropwise, a solution containing 6.0 g. (0.04 mole) of 2,7-dimethylindole in 30 ml. of anhydrous ether. When addition was complete, the reaction mixture was stirred at room temperature for one hour, then cooled in an ice bath and treated dropwise with a solution of 8.53 g. (0.05 mole) of 4-methoxybenzoyl chloride in 20 ml. of anhydrous ether. The mixture was stirred at room temperature for approximately twelve hours, then on a steam bath for two hours and then treated with ice water. Excess ammonium chloride was added, and the ether layer was separated, dried and evaporated to dryness to give a solid which was collected by filtration and washed thoroughly with water and ether to give 8.5 g. (76%) of 2,7-dimethyl-3-(4-methoxybenzoyl)indole, m.p. 182°–184° C.

Preparations 1B–1BN

Following a procedure similar to that described above in Preparation 1A, substituting for the 2,7-dimethylindole and the 4-methoxybenzoyl chloride used therein an appropriate 2-$R_2$-$R_4$-substituted-indole and an appropriate aroyl chloride ($R_3$CO-Cl), the following 2-$R_2$-$R_4$-substituted-3-arylcarbonyl indoles listed in Table A were prepared. In some instances the products, without further purification, were used directly in the next step of the synthesis of the final products of formula I, and no melting points were taken. In a few cases, the weight of the products was not obtained, and so calculation of yields of products in those instances are not possible. Here and elsewhere in the tables included with this specification, the melting point of the product (in °C. ) and the recrystallization solvent are given in columns headed "m.p./Solv.", and the yield, in percent, of product is given in columns headed "Yield".

TABLE A

| Prepn. | $R_2$ | $R_3$ | $R_4$ | m.p./Solv. | Yield |
|---|---|---|---|---|---|
| 1B | $CH_3$ | 4-$CH_3C_6H_4$ | — | 215–217/DMF-$H_2O$ | 85 |
| 1C | $CH_3$ | 4-$CH_3SC_6H_4$ | — | | |
| 1D | $CH_3$ | 4-$NO_2C_6H_4$ | — | | 23 |
| 1E | $CH_3$ | 4-$CH_3OC_6H_4$ | 5-F | 199–202/i-PrOH | |
| 1F | $CH_3$ | 4-$CH_3OC_6H_4$ | 7-F | 204–205/$H_2O$ | 42 |
| 1G | $CH_3$ | 4-$CH_3OC_6H_4$ | 7-$CH_3O$ | | 68 |
| 1H | $CH_3$ | 4-$CH_3OC_6H_4$ | 5-/7-F(a) | | 55 |
| 1I | $CH_3$ | 4-$FC_6H_4$ | — | 199–201/EtOH | 38 |
| 1J | $CH_3$ | 3,4-$OCH_2OC_6H_3$ | — | 210–213/i-PrOH | 60 |
| 1K | $CH_3$ | 3-benzo[b]thienyl | — | 181–183 | 64 |
| 1L | $CH_3$ | 2-benzo[b]furyl | — | 218–220/i-PrOH | 62 |
| 1M | $CH_3$ | 2-$CH_3OC_6H_4$ | — | 203–206/i-PrOH | 75 |
| 1N | $CH_3$ | 3-F-4-$CH_3OC_6H_3$ | — | 160–165/EtOH | 39 |
| 1-O | $CH_3$ | 2-naphthyl | — | 208–213/i-PrOH | 57 |
| 1P | H | 4-$CH_3OC_6H_4$ | 5-$CH_3$ | 189–192/EtOH | 42 |
| 1Q | $CH_3$ | 3-$FC_6H_4$ | — | | 64 |
| 1R | $CH_3$ | 2-$FC_6H_4$ | — | 216–218/i-PrOH | 44 |
| 1S | $CH_3$ | 4-$CNC_6H_4$ | — | 211–213/EtOAc | 7 |
| 1T | $CH_3$ | $C_6H_5$ | 4-$CH_3$ | 176–179/EtOAc | 65 |
| 1U | $CH_3$ | 4-$C_2H_5C_6H_4$ | — | 199–201/EtOAc | 70 |
| 1V | $CH_3$ | 3-$NO_2C_6H_4$ | — | 218–221/DMF-$H_2O$ | 20 |
| 1W | $CH_3$ | 4-$CH_3C_6H_4$ | — | 207–209/EtOH | 60 |
| 1X | $CH_3$ | 3-$CH_3OC_6H_4$ | — | 163–164/EtOAc | 63 |
| 1Y | H | 4-$CH_3OC_6H_4$ | — | | 46 |
| 1Z | H | $C_6H_5$ | 5-$CH_3O$ | | 46 |

TABLE A-continued

| Prepn. | R2 | R3 | R4 | m.p./Solv. | Yield |
|---|---|---|---|---|---|
| 1AA | CH3 | 4-CH3OC6H4 | 6-CH3O | | 53 |
| 1AB | CH3 | 4-NO2C6H4 | 6-CH3O | | 73 |
| 1AC | CH3 | C6H5 | — | 185–186/MeOH | 64 |
| 1AD | H | C6H5 | — | 241–242/MeOH | 38 |
| 1AE | CH3 | 4-ClC6H4 | — | 183–185/MeOH | 34 |
| 1AF | CH3 | 4-CH3OC6H4 | 6-Cl | | 58 |
| 1AG | CH3 | 4-CH3OC6H4 | 6-C6H5CH2O | | 51 |
| 1AH | CH3 | 2,3-OCH2OC6H3 | — | 239.5–240/CH3CN | 98 |
| 1AI | CH3 | 1-naphthyl | — | 223–224/i-PrOH | 69 |
| 1AJ | CH3 | 2,3-(CH3O)2C6H3 | — | 185–187 | 87 |
| 1AK | CH3 | 3,5-(CH3O)2C6H3 | — | 182–184 | 85 |
| 1AL | CH(CH3)2 | 4-CH3OC6H4 | — | 176–178/EtOAc-ether | 44 |
| 1AM | CH(CH3)2 | 4-CH3OC6H4 | 5-F | 173–175 | 11 |
| 1AN | CH3 | 2-FC6H4 | 5-F | 247–249/i-PrOH | 10 |
| 1AO | CH3 | 4-CH3O-1-naphthyl | — | 286–289/i-PrOH | 24 |
| 1AP | CH3 | 4-CH3OC6H4 | — | 200–203 | 97 |
| 1AQ | H | 1-naphthyl | 5-Br | 250–252/i-PrOH | 26 |
| 1AR | H | 4-CH3OC6H4 | 6-F | | 78 |
| 1AS | CH3 | 3,4,5-(CH3O)3C6H2 | — | | |
| 1AT | CH3 | 2,3,4-(CH3O)3C6H2 | — | | |
| 1AU | H | 1-naphthyl | 5-F | | 54 |
| 1AV | CH3 | 9-phenanthryl | — | 370(dec.)/EtOH | 51 |
| 1AW | CH3 | 1-anthryl | — | 280(dec.)/AcOH | 9 |
| 1AX | H | 4-ClC6H4 | — | 239–241 | 58 |
| 1AY | CH3 | 3,4-(CH3O)2C6H3 | — | 162–165/EtOAc | 19 |
| 1AZ | CH3 | 4-C2H5OC6H4 | — | 214–217/i-PrOH | 73 |
| 1BA | H | C6H5 | 7-CH3 | | 58 |
| 1BB | CH3 | 4-CH3OC6H4 | 4-F(b) | | 55 |
| 1BC | CH3 | 6-CH3O-2-naphthyl | — | | 40 |
| 1BD | CH3 | 1-naphthyl | 6-CH3 | 270–271/EtOH | 29 |
| 1BE | H | 1-naphthyl | — | | 87 |
| 1BF | CH3 | 4-CH3OC6H4 | — | 142–144/EtOAc | 59 |
| 1BG | H | 4-CH3OC6H4 | 5-F | 200–202 | 100 |
| 1BH | CH3 | C6H5 | 5-F | 223–225 | 67 |
| 1BI | CH3 | 4-CH3OC6H4 | 5-Cl | 167–169 | 41 |
| 1BJ | CH3 | 2,3-F2C6H3 | — | | |
| 1BK | CH3 | 2,6-(CH3)2C6H3 | — | | 95 |
| 1BL | CH3 | 4-CH3OC6H4 | 5,7-F2 | | 26 |
| 1BM | CH3 | 4-ClC6H4 | 6-CH3O | 206–208 | 61 |
| 1BN | CH3 | 3,4-Cl2C6H3 | — | 229–230 | 44 |

(a) Product consisted of a mixture of the 5-fluoro and the 7-fluoro isomers.
(b) Product consisted of a mixture of the 4- and 6-fluoro isomers.

B. The 2-R2-R4-Substituted-1-aminoalkyl-1H-indoles (a) By Alkylation of a 2-R2-R4-Substituted-indole Preparation 2A To a stirred suspension of 229.5 g. (1.22 moles) of 4-(2-chloroethyl)morpholine hydrochloride in 300 ml. of DMSO at ambient temperature was added 200 g. (3.03 moles) of 85% potassium hydroxide pellets, and the suspension was stirred for five minutes and then treated dropwise at ambient temperature with a solution of 133.7 g. (1.0 mole) of 2-methylindole in 140 ml. of DMSO. The temperature of the reaction mixture gradually rose during the addition of the 2-methylindole as well as on stirring after addition was complete. When the temperature reached 78° C., the mixture was cooled in a water bath until the temperature subsided to 75° C., and the mixture was stirred for a total of three and a half hours while the temperature subsided to ambient. The mixture was then diluted with 1 liter of water and extracted with toluene. The extracts were washed with water, dried over magnesium sulfate and taken to dryness in vacuo, and the residual dark oil was crystallized from heptane to give 224 g. (92%) of 2-methyl-1-[2-(4-morpholinyl)ethyl]-1H-indole, m.p. 63°–65° C.

Preparation 2B

Following a procedure similar to that described in Preparation 2A above, 60 g. (0.4 mole) isatin was reacted with 102 g. (0.54 mole) of 4-(2-chloroethyl)morpholine hydrochloride in 100 ml. of dry DMF in the presence of 120 g. (0.87 mole) of potassium carbonate to give 52 g. of 1-[2-(4-morpholinyl)ethyl]-2,3-dioxo-1H-indole.

The latter (0.2 mole) was dissolved in 200 ml. of MDC and the solution treated all at once with 40 ml. of phosphorus oxychloride and then treated dropwise with cooling with 55 g. of phosphorus pentachloride. The reaction mixture was stirred at ambient temperature for about forty-eight hours and then added dropwise with stirring to 500 ml. of 3N hydrochloric acid containing zinc dust, additional zinc dust being added with addition of the reaction mixture, a total of 168 g. of zinc dust being added. The reaction mixture was then stirred at ambient temperature for about one hour, filtered, the filter washed several times with water and the combined filtrates evaporated to remove the MDC. The mixture was filtered, the filtrate neutralized by the addition of solid potassium carbonate, and the resulting mixture extracted with ethyl acetate. The combined extracts, on drying and evaporation to dryness, afforded 29.2 g. of 1-[2-(4-morpholinyl)ethyl]-2-oxo-1H-indole, as an oil.

A mixture of the latter (40 g., 0.139 mole) and 100 ml. of phosphorus oxychloride was heated on the steam bath for several days and the reaction mixture then taken to dryness in vacuo. The residue was dissolved in MDC, and the solution poured slowly onto an ice-/potassium carbonate/ethyl acetate mixture. The organic layer was separated from the mixture, dried and taken to dryness and the residue taken into a 15% solution of ethyl acetate in toluene and the solution chromatographed on silica gel, the product being eluted with the same solution. The initial cuts were discarded and the final cuts combined and evaporated to dryness to give the product in the form of the free base which was converted to the hydrochloride salt to give 9.9 g. of 2-chloro-1-[2-(4-morpholinyl)ethyl]-1H-indole hydrochloride.

Preparations 2C-2-O

Following a precedure similar to that described in Preparation 2A above, substituting for the N-(2-chloroethyl)morpholine hydrochloride and the 2-methylindole used therein an appropriate N-(haloalkyl)morpholine and an appropriate 2-$R_2$-$R_4$-substituted-indole, the following 2-$R_2$-$R_4$-substituted-1-[(4-morpholinyl)alkyl]-1H-indoles listed in Table B were prepared.

TABLE B

| Prepn. | $R_2$ | $R_4$ | Alk | m.p./Solv. | Yield |
|---|---|---|---|---|---|
| 2C | H | — | CH$_2$CH$_2$ | — | 46 |
| 2D | CH$_3$ | 7-CH$_3$O | CH$_2$CH$_2$ | — | 31 |
| 2E | H | 5-F | (CH$_2$)$_3$ | oil b.p. 150-170/ 0.01 mm. | 84 |
| 2F | H | 5-F | CH$_2$CH$_2$ | oil b.p. 153-159/ 0.04 mm. | 92 |
| 2G | H | 6-F | (CH$_2$)$_3$ | 152-154 (HCl) MDC/Et$_2$O | 81 |
| 2H | H | — | (CH$_2$)$_3$ | yellow oil | 66 |
| 2I | H | 6-CH$_3$ | CH$_2$CH$_2$ | yellow oil | 100 |
| 2J | H | 5-BzO | CH$_2$CH$_2$ | oil | 80 |
| 2K | H | 4-BzO | CH$_2$CH$_2$ | — | 98 |
| 2L | H | 7-BzO | CH$_2$CH$_2$ | — | 75 |
| 2M | CH$_3$ | 5-F | (CH$_2$)$_3$ | 165-167(c) | 81 |
| 2N | CH$_3$ | 5-F | CH$_2$CH$_2$ | oil | 100 |
| 2-O | C$_2$H$_5$ | — | CH$_2$CH$_2$ | 59-60/hexane | 54 |

(c) Maleate (b) Via the 2-$R_2$-$R_4$-Substituted-1H-indole-alkanamides

Preparation 3A

Following a procedure similar to that described in Preparation 2A above, 32.8 g. (0.25 mole) of 2-methylindole in 160 ml. of dry DMF was reacted with 13.4 g. (0.28 mole) of a 50% mineral oil dispersion of sodium hydride in 200 ml. of dry DMF, and the resulting sodium salt was then reacted with 62 g. (0.28 mole) of 4-(α-bromopropionyl)morpholine in 160 ml. of DMF to give 55.3 g. (59%) of 4-[α-(2-methyl-1H-indol-1-yl)-propionyl]morpholine.

The latter (130 g., 0.48 mole), dissolved in 900 ml. of THF, was added to 80 ml. (0.80 mole) of a solution of boron methyl sulfide complex in THF under nitrogen while cooling in an ice bath. When addition was complete, the mixture was stirred for eighteen hours at room temperature, heated under reflux for four hours, quenched by addition of about 1 liter of methanol, boiled for about fifteen minutes, concentrated essentially to dryness and then diluted with aqueous 6N hydrochloric acid. The mixture was extracted with methylene dichloride, and the raffinate was basified with 35% sodium hydroxide and extracted with ethyl acetate. The combined organic extracts were washed with brine, dried and concentrated to dryness to give 42.6 g. (34%) of 2-methyl-1-[I-methyl-2-(4-morpholinyl)ethyl]-1H-indole as an oil. A portion of the latter was reacted with methanesulfonic acid to give the monomethanesulfonate as the 4:1 hydrate, m.p. 154°-157° C.

Preparation 3B

Following a procedure similar to that described in Preparation 3A above, 29.29 g. (0.25 mole) of indole in 200 ml. of dry DMF was reacted with 13.4 g. (0.28 mole) of a 50% mineral oil dispersion of sodium hydride in 200 ml. of dry DMF and the resulting sodium salt reacted with 62.0 g. (0.28 mole) of 4-(α-bromopropionyl)morpholine in 200 ml. of dry DMF and the product recrystallized from isopropanol to give 13.7 g. (21%) of 4-[α-(1H-indole-1-propionyl]morpholine, m.p. 92°-94° C. The latter (20 g., 0.078 mole) in 300 ml. of diethyl ether was reduced with 3.12 g. (0.078) mole of lithium aluminum hydride in 100 ml. of diethyl ether to give 17 g. (90%) of 1-[1-methyl-2-(4-morpholinyl)ethyl]-1H-indole, m.p. 35°-37° C.

Preparation 3C

Following a procedure similar to that described in Preparation 3B, 83 g. (0.63 mole) of 2-methylindole was reacted with 30 g. (0.75 mole) of a 60% mineral oil dispersion of sodium hydride, and the resulting sodium salt was reacted with a molar equivalent amount of 4-(α-bromobutyryl)-morpholine in 100 ml. of DMF. The crude product thus obtained was reduced with 25 g. (0.66 mole) of lithium aluminum hydride in 500 ml. of THF. The product was isolated in the form of the hydrochloride to give 53.4 g. (27%) of 2-methyl-1-[1-ethyl-2-(4-morpholinyl)ethyl]-1-H-indole hydrochloride, m.p. 159°-162° C. (from ethyl acetate-ether).

Preparation 3D

Following a procedure similar to that described in Preparation 3A above, 25 g. (0.19 mole) of 7-methylindole in 150 ml. of dry DMF was reacted with 8.6 g. (0.21 mole) of a 60% mineral oil dispersion of sodium hydride in 150 ml. of dry DMF and the resulting sodium salt reacted with 65 g. (0.21 mole) of 4-(α-bromopropionyl)morpholine in 150 ml. of DMF to give 40.5 g. of 4-[α-(7-methyl-1H-indol-1-yl)propionyl]morpholine. The latter (0.15 mole) in 200 ml. of diethyl ether was reduced with 5.6 g. (0.15 mole) of lithium aluminum hydride in 200 ml. of diethyl ether to give 26.3 g. (68%) of 1-[1-methyl-2-(4-morpholinyl)ethyl]-7-methyl-1H-indole as a yellow oil.

C. The 2-$R_2$-$R_4$-Substituted-3-$R_3$-carbonyl-1-halo- or tosyloxyalkyl-1H-indoles

Preparation 4A

To a suspension of 24.8 g. (0.087 mole) of 2-methyl-3-(1-naphthylcarbonyl)indole (Preparation 1AM) in 300 ml. of THF was added, dropwise with stirring, 35 ml. (0.09 mole) of a 2.6M solution of n-butyl lithium in hexane while maintaining the temperature at 2°-4° C. The reaction mixture was stirred for one and a quarter hours at 2°-4° C., then at room temperature for forty-five minutes, recooled to 0° C. and treated dropwise, over a forty minute period, with a solution of 5.6 ml.

(0.15 mole) of a 2.6M solution of ethylene oxide in THF. The reaction mixture was gradually allowed to warm to room temperature, treated with a saturated ammonium chloride solution and the aqueous layer extracted with ethyl acetate. The combined organic extracts were evaporated to dryness in vacuo, and the residual solid was recrystallized from cyclohexane to give 22.6 g. of 2-methyl-3-(1-naphthylcarbonyl)-1-(2-hydroxyethyl)-1H-indole (64%).

Reaction of the latter (0.065 mole) with 18.5 g. (0.097 mole) of p-toluenesulfonyl chloride in 400 ml. of methylene dichloride in the presence of 340 ml. of 35% sodium hydroxide and 0.6 g. (0.0026) mole of benzyl trimethyl ammonium chloride afforded 20.1 g. (64%) of 2-methyl-3-(1-naphthylcarbonyl)-1-(2-p-toluenesulfonyloxyethyl)-1H-indole as a viscous oil.

Preparation 4B

Following a procedure similar to that described above in Preparation 4A, 40 g. (0.015 mole) of 2-methyl-3-(4-methoxybenzoyl)indole in 320 ml. of THF was reacted with 61 ml. of a 2.6M solution of butyl lithium in hexane and 45.8 ml. of ethylene oxide to give 33.6 g. (72%) of 2-methyl-3-(4-methoxybenzoyl)-1-(2-hydroxyethyl)-1H-indole. Reaction of 17 g. (0.06 mole) of the latter with 72 g. (0.06 mole) of p-toluenesulfonyl chloride in 250 ml. of pyridine afforded 2-methyl-3-(4-methoxybenzoyl)-1-(2-p-toluenesulfonyloxyethyl)-1H-indole as an oil.

Preparation 4C

Following a procedure similar to that described in Preparation 4A above, 75 g. (0.26 mole) of 2-methyl-3-(1-naphthylcarbonyl)indole in 900 ml. of THF was reacted with 105 ml. of a 2.6M solution of butyl lithium in hexane and 98 ml. of ethylene oxide to give 101.1 g. of 2-methyl-3-(1-naphthylcarbonyl)-1-(2-hydroxyethyl)-1H-indole as an amber oil, 21.3 g. (0.0647 mole) of which in 200 ml. of MDC, together with 0.6 g. of benzyl trimethyl ammonium chloride and 40 ml. of 35% sodium hydroxide was treated with 18.5 g. (0.097 mole) of p-toluenesulfonyl chloride in MDC. There was thus obtained 20.1 g. (64%) of 2-methyl-3-(1-naphthylcarbonyl)-1-(2-p-toluenesulfonyloxyethyl)-1H-indole as an amber oil.

Preparation 4D

Following a procedure similar to that described above in Preparation 4A, 20 g. (0.1 mole) of 2-methyl-3-(4-ethylbenzoyl)indole in 200 ml. of THF was reacted with 51 ml. of a 2.15M solution of n-butyl lithium in hexane and 6.16 g. of ethylene oxide to give 18 g. (73%) of 2-methyl-3-(4-ethylbenzoyl)-1-(2-hydroxyethyl)-1H-indole, which was dissolved in 480 ml. of MDC and 50 ml. of 35% sodium hydroxide and reacted with 14.32 g. of p-toluenesulfonyl chloride in the presence of 1.6 g. of benzyl trimethyl ammonium chloride. There was thus obtained 25 g. of 2-methyl-3-(4-ethylbenzoyl)-1-(2-p-toluenesulfonyloxyethyl)-1-H-indole.

Preparation 4E

A solution of 120 g. (0.42 mole) of 5-fluoro-2-methyl-3-(4-methoxybenzoyl)indole in 240 ml. of DMF was treated first with 427 g. (2.12 mole) of 1,3-dibromopropane and then with 25.8 g. of a 60% mineral oil dispersion of sodium hydride added in portions while cooling in an ice bath. The mixture was stirred for about twelve hours, taken to dryness and the residue partitioned between MDC and water. The organic layer was separated, washed with water, dried and taken to dryness and the residue recrystallized from ethyl acetate/hexane to give 51 g. (30%) of 5-fluoro-2-methyl-3-(4-methoxybenzoyl)-1-(3-bromopropyl)-1H-indole, m.p. 131°–134°.

Preparation 4F

Following a procedure similar to that described in Preparation 4E above, 100 g. (0.38 mole) of 2-methyl-3-(4-methoxybenzoyl)-1H-indole in 250 ml. of DMF was reacted with 22.6 g. (0.57 mole) of a 60% mineral oil dispersion of sodium hydride and 381 g. (1.9 mole) of 1,3-dibromopropane to give 30 g. (21%) of 2-methyl-3-(4-methoxybenzoyl)-1-(3-bromopropyl)-1H-indole.

Preparation 4G

Following a procedure similar to that described in Preparation 4E above, 15 g. (0.053 mole) of 5-fluoro-2-methyl-3-(4-methoxybenzoyl)indole in 200 ml. of DMF was reacted with 3.1 g. of a 60% mineral oil dispersion of sodium hydride and 9.18 g. (0.058 mole) of 1-bromo-3-chloropropane to give 15.3 g. (80%) of 5-fluoro-2-methyl-3-(4-methoxybenzoyl)-1-(3-chloropropyl)-1H-indole.

Preparation of the Final Products

A. From the 2-$R_2$-$R_4$-Substituted-3-$R_3$-carbonylindoles

Example 1A

Following a procedure similar to that described in Preparation 2A above, 25 g. (0.10 mole) of 3-(4-methoxybenzoyl)indole (Preparation 1Y) in 100 ml. of DMF was reacted with 5.76 g. (0.12 mole) of a 50% dispersion of sodium hydride in mineral oil in 120 ml. of DMF, and the resulting sodium salt was reacted with 0.14 mole of 4-(2-chloroethyl)-morpholine (freed from 26.06 g. of the corresponding hydrochloride) in 120 ml. of DMF to give 42 g. of the crude product as an oil which, on trituration with ethyl acetate/diethyl ether/hexane, gave a yellow crystalline solid which was converted to the methanesulfonate salt to afford 9.5 g. (20%) of 3-(4-methoxybenzoyl)-1-[2-(4-morpholinyl)ethyl]1H-indole methanesulfonate monohydrate, m.p. 110°–112° C.

Examples 1B–1CJ

Following a procedure similar to that described in Example 1A above, the following species of formula I in Table 1 were prepared by reaction of a 2-$R_2$-$R_4$-substituted-3-$R_3$-carbonyl-1H-indole with an appropriate haloalkylamine or tosyloxyalkylamine. The acid-acceptor and reaction solvent used in the reactions are given in the column headed "Cat./Solv.". Here and elsewhere in the tables, the form in which the product was isolated, either as the free base or as an acid-addition salt, is given in columns headed "Base/Salt", and the abbreviations "Morph.", "Pip." and "Pyr." in the columns headed N=B represent the 4-morpholinyl, 1-piperidinyl and 1-pyrrolidinyl groups, respectively. In Table 1, unless noted otherwise, an appropriate chloroalkylamine was used as the alkylating agent. Here and elsewhere in the specification and the claims, the alkylene groups, Alk, are depicted as they would appear with the 1-indolyl moiety attached to the carbon atom at the left end of the alkylene chain and with the amine group, N=B, attached to the carbon at the right end of the chain.

TABLE 1

| Example | R₂ | R₃ | R₄ | Alk | N B | Cat./Solv. | Base/Salt | m.p./Solv. | Yield |
|---|---|---|---|---|---|---|---|---|---|
| 1B | CH₃ | 4-CH₃OC₆H₄ | — | (CH₂)₂ | Morph. | K₂CO₃/DMF | Base(d) | 104–105/EtOAc-hexane | 37 |
| 1C | CH₃ | 4-CH₃SC₆H₄ | — | (CH₂)₂ | Morph. | K₂CO₃/DMF | Base | 125–126/EtOAc-hexane | 36 |
| 1D | CH₃ | 4-CH₃OC₆H₄ | 7-CH₃ | (CH₂)₂ | Morph. | NaH/DMF | Base | 149–151/i-PrOH | 83 |
| 1E | CH₃ | 4-CH₃OC₆H₄ | 5-F | (CH₂)₂ | Morph. | NaH/DMF | HCl | 198–200/MeOH-ether | 59 |
| 1F | CH₃ | 4-CH₃OC₆H₄ | — | (CH₂)₂ | Morph. | NaH/DMF | HCl | 248–249/MeOH-ether | 53 |
| 1G | CH₃ | 4-CH₃OC₆H₄ | 5-F | (CH₂)₂ | Morph. | NaH/DMF | HCl | 222–224/i-PrOH-ether | 50 |
| 1H | CH₃ | 4-CH₃OC₆H₄ | — | (CH₂)₃ | Morph. | NaH/DMF | HCl | 202–203/i-PrOH-ether | 53 |
| 1I | CH₃ | 4-CH₃OC₆H₄ | — | (CH₂)₂ | Pip. | NaH/DMF | CH₃SO₃H | 228–230/MeOH-ether | 31 |
| 1J | CH₃ | 4-CH₃OC₆H₄ | 7-F | (CH₂)₂ | Morph. | NaH/DMF | Base | 120–121/i-PrOH | 23 |
| 1K | CH₃ | 4-CH₃OC₆H₄ | 7-CH₃O | (CH₂)₂ | Morph. | NaH/DMF | HCl | 203–204 | 25 |
| 1L | CH₃ | 4-CH₃OC₆H₄ | 6-Cl | (CH₂)₂ | Morph. | NaH/DMF | Base | 138–139/i-PrOH | 3 |
| 1M | CH₃ | 4-CH₃OC₆H₄ | 4-/6-F(e) | (CH₂)₂ | Morph. | NaH/DMF | Base | 127–128/DMF | 39 |
| 1N | CH₃ | 4-FC₆H₄ | — | (CH₂)₂ | Morph. | K₂CO₃/DMF | CH₃SO₃H | 209–211/i-PrOH | 70 |
| 1-O | CH₃ | 3,4-OCH₂OC₆H₃ | — | (CH₂)₂ | Morph. | K₂CO₃/DMF | CH₃SO₃H | 142–145/i-PrOH | 33 |
| 1P | CH₃ | 2-benzo[b]furyl | — | (CH₂)₂ | Morph. | K₂CO₃/DMF | CH₃SO₃H | 194–198/EtOH | 60 |
| 1Q | CH₃ | 3-benzo[b]thienyl | — | (CH₂)₂ | Morph. | K₂CO₃/DMF | CH₃SO₃H.H₂O | 155–158/EtOH | 55 |
| 1R | CH₃ | 2-CH₃OC₆H₄ | — | (CH₂)₂ | Morph. | K₂CO₃/DMF | CH₃SO₃H | 199–214/i-PrOH | 65 |
| 1S | H | 2-naphthyl | — | (CH₂)₂ | Morph. | K₂CO₃/DMF | CH₃SO₃H | 195–198/i-PrOH | 35 |
| 1T | CH₃ | 4-CH₃OC₆H₄ | 5-CH₃ | (CH₂)₂ | Morph. | K₂CO₃/DMF | CH₃SO₃H | 150–151/i-PrOH | 45 |
| 1U | H | 3-FC₆H₄ | — | (CH₂)₂ | Morph. | K₂CO₃/DMF | Base | 130–131/i-PrOH | 77 |
| 1V | CH₃ | 2-FC₆H₄ | 4-CH₃ | (CH₂)₂ | Morph. | K₂CO₃/DMF | Base | 112–114/i-PrOH | 65 |
| 1W | CH₃ | C₆H₅ | — | (CH₂)₂ | Morph. | K₂CO₃/DMF | Base | 116–117.5/EtOH | 46 |
| 1X | CH₃ | 4-C₂H₅C₆H₄ | — | (CH₂)₂ | Morph. | K₂CO₃/DMF | Base | 124–126/EtOAc | 70 |
| 1Y | CH₃ | 3-NO₂C₆H₄ | — | (CH₂)₂ | Morph. | K₂CO₃/DMF | Base | 141–143/EtOAc | 67 |
| 1Z | CH₃ | 3-CH₃OC₆H₄ | — | (CH₂)₂ | Morph. | K₂CO₃/DMF | Base | 120.5–121.5/EtOAc | 60 |
| 1AA | CH₃ | 3,4-(CH₃O)₂C₆H₃ | — | (CH₂)₂ | Morph. | K₂CO₃/DMF | Base | 130–131/EtOAc | 84 |
| 1AB | H | C₆H₅ | — | (CH₂)₂ | Morph. | K₂CO₃/DMF | HCl | 230–233/EtOH | 64 |
| 1AC | CH₃ | C₆H₅ | 5-CH₃O | (CH₂)₂ | Morph. | K₂CO₃/DMF | Base | 98–101 | 55 |
| 1AD | CH₃ | 4-CH₃OC₆H₄ | 6-CH₃O | (CH₂)₂ | Morph. | NaH/DMF | Base | 222–224/EtOAc-MDC-ether | 63 |
| 1AE | CH₃ | C₆H₅ | — | CHCH₃CH₂ | Morph. | NaH/DMF | HCl | 111–112/EtOAc-hexane | 78 |
| 1AF | CH₃ | C₆H₅ | — | CH₂CHCH₃ | Morph. | NaH/DMF | Base | 101–103/EtOAc-hexane | 69 |
| 1AG | H | C₆H₅ | — | CH₂CHCH₃ | Morph. | K₂CO₃/DMF | Base | 148–150/EtOAc | 54 |
| 1AH | CH₃ | 4-ClC₆H₄ | — | (CH₂)₂ | Morph. | K₂CO₃/DMF | Base | 136–138/EtOAc-hexane | 60 |
| 1AI | H | 4-ClC₆H₄ | — | (CH₂)₂ | Morph. | K₂CO₃/DMF | HCl | 128–130/EtOAc-hexane | 44 |
| 1AJ | CH₃ | 3,4-Cl₂C₆H₃ | — | (CH₂)₂ | Morph. | K₂CO₃/DMF | Base | 275–285/EtOH-H₂O | 52 |
| 1AK | CH₃ | C₆H₅ | 6-CH₃O | (CH₂)₂ | Morph. | K₂CO₃/DMF | Base | 137–139/EtOAc-hexane | 1.3 |
| 1AL(f) | CH₃ | C₆H₅ | — | (CH₂)₂ | Morph. | K₂CO₃/DMF | Base | 108–110/EtOAc-hexane | 48 |
| 1AM(g) | CH₃ | C₆H₅ | — | (CH₂)₂ | N(CH₃)₂ | NaH/DMF | HCl | 123–125/EtOAc-hexane | 7 |
| 1AN(g) | H | C₆H₅ | — | (CH₂)₂ | N(C₂H₅)₂ | NaH/DMF | Base.H₂O | 97–100/EtOH-hexane | 48 |
| 1AO | CH₃ | 1-naphthyl | — | (CH₂)₂ | Morph. | K₂CO₃/DMF | Base | 131–133/EtOAc-hexane | 80 |
| 1AP | CH₃ | C₆H₅ | 7-CH₃ | (CH₂)₂ | Morph. | K₂CO₃/DMF | Base | 122–124/i-PrOH | 40 |
| 1AQ | CH₃ | 4-CH₃OC₆H₄ | — | (CH₂)₂ | Morph. | NaH/DMF | HCl | 237–241/MeOh | 56 |
| 1AR | CH₃ | C₆H₅ | — | (CH₂)₂ | Morph. | NaH/DMF | HCl | 209–211/EtOAc-ether | 62 |
| 1AS | CH₃ | 4-PrOC₆H₄ | — | (CH₂)₂ | Morph. | NaH/DMF | Base | 127–128/DMF | 38 |
| 1AT | CH₃ | 4-EtOC₆H₄ | — | (CH₂)₂ | Morph. | K₂CO₃/DMF | Base | 104.5–105.5/i-PrOH | 39 |
| 1AU | H | C₆H₅ | — | (CH₂)₂ | Morph. | K₂CO₃/DMF | Base | 93–97/i-PrOH | 68 |
| 1AV | CH₃ | 4-CH₃O-1-naphthyl | — | (CH₂)₂ | Morph. | K₂CO₃/DMF | CH₃SO₃H.0.4i-PrOH | 145–147/i-PrOH | 26 |
| 1AW | CH₃ | 6-CH₃O-2-naphthyl | — | (CH₂)₂ | Morph. | K₂CO₃/DMF | Base | 159–160/EtOAc | 4.9 |

TABLE 1-continued

| Example | R₂ | R₃ | R₄ | Alk | N―B | Cat./Solv. | Base/Salt | m.p./Solv. | Yield |
|---|---|---|---|---|---|---|---|---|---|
| IAX | H | 4-CH₃OC₆H₄ | 5-F | (CH₂)₃ | Morph. | NaH/DMF | HCl | 172-174/i-PrOH | 67 |
| IAY | CH₃ | 4-CH₃OC₆H₄ | 5-F | (CH₂)₃ | Pip. | NaH/DMF | HCl | 199-201/MeOH-ether | 40 |
| IAZ | CH₃ | C₆H₅ | 5-F | (CH₂)₃ | Morph. | NaH/DMF | HCl | 244-245/MeOH-ether | 81 |
| IBA | CH₃ | 4-CH₃OC₆H₄ | 5-F | (CH₂)₃ | N(C₂H₅)₂ | NaH/DMF | HCl | 124-126/MeOH-ether | 52 |
| IBB | CH₃ | 4-CH₃OC₆H₄ | 5-Cl | (CH₂)₃ | Morph. | NaH/DMF | HCl | 160-162/MeOH-ether(h) | 64 |
| IBC | CH₃ | 4-CH₃OC₆H₄ | 5,7-F | (CH₂)₃ | Morph. | NaH/DMF | HCl | 231-233/i-PrOH | 79 |
| IBD | CH₃ | 4-CH₃OC₆H₄ | 7-F | (CH₂)₃ | Morph. | NaH/DMF | HCl | 209-211/MDC-ether | 59 |
| IBE | CH₃ | 4-CH₃OC₆H₄ | 5-F | CHCH₃—CH₂CH₂ | Morph. | NaH/DMF | HCl | 178-180/i-PrOH-ether | 72 |
| IBF | CH₃ | 2-FC₆H₄ | — | CH₂CHCH₃ | Morph. | NaH/DMF | Base | 107-109 | 53 |
| IBG | CH₃ | 4-CH₃OC₆H₄ | — | CH₂CHCH₃ | Morph. | NaH/DMF | Base | 128-130/EtOAc-hexane | 45 |
| IBH | CH₃ | 2-FC₆H₄ | 5-F | CHCH₃—CH₂CH₂ | Morph. | NaH/DMF | Base | 124-126/EtOAc-hexane | 50 |
| IBI | CH₃ | 4-CH₃OC₆H₄ | — | CHCH₃—CH₂CH₂ | Morph. | NaH/DMF | HCl | 164-166/MeOH-ether | 24 |
| IBJ | CH₃ | 2,3-OCH₂OC₆H₃ | — | CH₂CH₂ | Morph. | K₂CO₃/DMF | Base | 173-174/CHCl₃ | 81 |
| IBK | CH₃ | 2-FC₆H₄ | — | CHCH₃—CH₂CH₂ | Morph. | NaH/DMF | HCl.½H₂O | 147-150/MDC-ether | 36 |
| IBL | CH₃ | 2-naphthyl | — | CH₂CH₂ | N(C₂H₅)₂ | NaH/DMF | Base | 106-107/EtOH | 34 |
| IBM | H | C₆H₅ | — | (CH₂)₂ | N(CH₃)₂ | NaH/DMF | Base | 65-67 | 43 |
| IBN | CH₃ | 2,3-F₂C₆H₃ | — | (CH₂)₂ | Morph. | NaH/DMF | HCl | 165-167/MDC | 37 |
| IBO | CH₃ | 2,6-(CH₃)₂C₆H₃ | — | (CH₂)₂ | Morph. | NaH/DMF | Base | 275-280 | 100 |
| IBP | CH₃ | 2,3-(CH₃O)₂C₆H₃ | — | (CH₂)₂ | Morph. | NaH/DMF | Base | 126-128 | 77 |
| IBQ | CH₃ | 3,5-(CH₃O)₂C₆H₃ | — | (CH₂)₂ | Morph. | NaH/DMF | Base | 88-90 | 64 |
| IBR | CH(CH₃)₂ | 4-CH₃OC₆H₄ | — | (CH₂)₂ | Morph. | NaH/DMF | Base | 151-153/EtOAc-hexane | 42 |
| IBS | CH(CH₃)₂ | 4-CH₃OC₆H₄ | — | (CH₂)₃ | Morph. | NaH/DMF | Base | 90-92 | 42 |
| IBT | CH₃ | 4-NO₂C₆H₄ | — | (CH₂)₃ | Morph. | NaH/DMF | Base | 173-175 | 49 |
| IBU | CH₃ | 1-naphthyl | — | (CH₂)₂ | Morph. | NaH/DMF | Base | 135-138/ether | 50 |
| IBV | CH₃ | 1-naphthyl | 6-CH₃ | (CH₂)₂ | Morph. | K₂CO₃/DMF | Base | 154.5-156/EtOAc | 74 |
| IBW | H | 1-naphthyl | 5-Br | (CH₂)₂ | Morph. | K₂CO₃/DMF | Base | 153-155/EtOAc | 37 |
| IBX | CH₃ | 1-naphthyl | — | CH₂CHCH₃ | Morph. | NaH/DMF | Base | 145-147/EtOAc-hexane | 35 |
| IBY | H | 4-CH₃OC₆H₄ | 6-F | (CH₂)₃ | Morph. | NaH/DMF | Base | 190-192/MeOH-ether | 7 |
| IBZ | CH₃ | 4-CH₃OC₆H₄ | — | (CH₂)₂ | Morph. | NaH/DMF | HCl.½H₂O | 131-135/EtOAc-hexane | 31 |
| ICA | CH₃ | 2,3,4-(CH₃O)₃C₆H₂ | — | (CH₂)₂ | Morph. | NaH/DMF | Base | 127-128/EtOAc | 80 |
| ICB | CH₃ | 3,4,5-(CH₃O)₃C₆H₂ | — | (CH₂)₂ | Morph. | NaH/DMF | HCl | 156-158/EtOH-ether | 30 |
| ICC | H | 4-CH₃OC₆H₄ | 7-CH₃ | (CH₂)₂ | Morph. | NaH/DMF | Base | 146-149/EtOAc-hexane | 75 |
| ICD | H | 1-naphthyl | 7-CH₃ | (CH₂)₂ | Morph. | NaH/DMF | Base | 139-142 | 44 |
| ICE | H | 1-anthryl | 5-F | (CH₂)₂ | Morph. | NaH/DMF | CH₃SO₃H | 210-212 | 67 |
| ICF | CH₃ | 9-phenanthryl | — | (CH₂)₂ | Morph. | KOH/DMSO | Base | 126-128 | 62 |
| ICG | CH₃ | C₆H₅ | — | (CH₂)₂ | Morph. | KOH/DMSO | HCl | 180-182/CHCl₃-ether | 42 |
| ICH | H | 4-CH₃OC₆H₄ | — | (CH₂)₂ | Pyr. | NaH/DMF | Base | 76-78/EtOAc-hexane | 41 |
| ICI | CH₃ | 4-CH₃OC₆H₄ | — | (CH₂)₂ | Pyr. | NaH/DMF | HCl | 233-235/MeOH-ether | 77 |
| ICJ | CH₃ | 4-CH₃OC₆H₄ | — | (CH₂)₃ | Pyr. | NaH/DMF | CH₃SO₃H | 152-153/i-PrOH | 77 |

(d) The corresponding methanesulfonate has m.p. 162-164 (from isopropanol) has m.p. 146-149 (from methanol-ether). A higher melting polymorph of the maleate, m.p. 163-166, was obtained on crystallization from methanol alone.
(e) Consists of a 4:1 mixture of the 4-fluoro and 6-fluoro isomers.
(f) Prepared by reaction of 4-(2-tosyloxypropyl)morpholine with appropriate indole.
(g) Prepared by reaction of 4-(bromopropyl)morpholine with appropriate indole.
(h) A higher melting polymorph of the hydrochloride has m.p. 217-218 from isopropanol.

B. From the 2-R$_2$-R$_4$-Substituted-1H-indoles

Example 2A

To a stirred, refluxing solution of 13.2 g. (0.054 mole) of 1-[1-methyl-2-(4-morpholinyl)ethyl]-1H-indole (Preparation 3B) in 150 ml. of ethylene dichloride was added, over a period of about one hour, a mixture of 17.35 g. (0.13 mole) of aluminum chloride and 10.08 g. (0.065 mole) of 4-methylbenzoyl chloride in 200 ml. of ethylene dichloride. When addition was complete, the mixture was heated under reflux under a nitrogen atmosphere for three and a half hours and then poured, with stirring, into 1 liter of ice and water containing 300 ml. of 5N sodium hydroxide. The mixture was transferred to a separatory funnel, the organic layer was separated, and the aqueous layer was washed with an additional 300 ml. of ethylene dichloride. The combined organic extracts were then washed with brine, filtered, dried over magnesium sulfate, filtered again and evaporated to dryness to give a viscous oil (22.55 g.) which solidified on cooling. The latter was recrystallized, after charcoaling, from isopropanol to give 15.78 g. (81%) of 3-(4-methylbenzoyl)-1-[1-methyl-2-(4-morpholinyl)ethyl]-1H-indole, m.p. 116.5°–118° C.

Examples 2B–2CJ

Following a procedure similar to that described in Example 2A above, the following species of formula I in Table 2 below were prepared by reaction of a 2-R$_2$-R$_4$-substituted-1-aminoalkyl-1H-indole with an appropriate acid chloride (R$_3$CO—Cl) in the presence of aluminum chloride. The solvent used to carry out the reaction, methylene dichloride (MDC) or ethylene dichloride (EDC), is given in the column headed "Solv."

TABLE 2

| Example | R$_2$ | R$_3$ | R$_4$ | Alk | N=B | Solv. | Base/Salt | m.p./Solv. | Yield |
|---|---|---|---|---|---|---|---|---|---|
| 2B | CH$_3$ | 4-CH$_3$C$_6$H$_4$ | — | CHCH$_3$CH$_2$ | Morph. | EDC | Base | 163–165/i-PrOH | 69 |
| 2C | CH$_3$ | 2-FC$_6$H$_4$ | — | CHCH$_3$CH$_2$ | Morph. | EDC | Base | 126–128/i-PrOH | 62 |
| 2D | H | 4-FC$_6$H$_4$ | — | CHCH$_3$CH$_2$ | Morph. | EDC | Base | 153–155/i-PrOH | 83 |
| 2E | H | 2-FC$_6$H$_4$ | — | CHCH$_3$CH$_2$ | Morph. | EDC | Base | 145–147/i-PrOH | 65 |
| 2F | CH$_3$ | 4-FC$_6$H$_4$ | — | CHCH$_3$CH$_2$ | Morph. | EDC | Base | 95–98/heptane | 23 |
| 2G | CH$_3$ | 4-CH$_3$OC$_6$H$_4$ | — | CHCH$_3$CH$_2$ | Morph. | EDC | Base(i) | yellow-orange powder | 13 |
| 2H | H | C$_6$H$_5$ | 7-CH$_3$ | CHCH$_3$CH$_2$ | Morph. | EDC | HCl.¼C$_2$H$_5$OH | amorphous, off white solid | 62 |
| 2I | CH$_3$ | 4-t-C$_4$H$_9$C$_6$H$_4$ | — | (CH$_2$)$_2$ | Morph. | MDC | HCl | 235–236 | 57 |
| 2J | CH$_3$ | 2-benzo[b]thienyl | — | (CH$_2$)$_2$ | Morph. | MDC | Base | 134–135 | 23 |
| 2K | CH$_3$ | 2-CH$_3$C$_6$H$_4$ | — | (CH$_2$)$_2$ | Morph. | MDC | HCl | 245–247/i-PrOH-ether | 25 |
| 2L | CH$_3$ | 3,4-(CH$_3$)$_2$C$_6$H$_3$ | — | (CH$_2$)$_2$ | Morph. | MDC | Base | 145–147/i-PrOH | 41 |
| 2M | CH$_3$ | C$_6$H$_5$CH=CH$_2$ | — | (CH$_2$)$_2$ | Morph. | MDC | Base | 127–128/EtOH | 29 |
| 2N | CH$_3$ | 3-benzo[b]furyl | — | (CH$_2$)$_2$ | Morph. | MDC | Base | 134–135/EtOH | 28 |
| 2O | H | 2-CH$_3$C$_6$H$_4$ | — | (CH$_2$)$_2$ | Morph. | MDC | Base | 129–131/i-PrOH | 100 |
| 2P | C$_2$H$_5$ | 4-CH$_3$OC$_6$H$_4$ | — | (CH$_2$)$_2$ | Morph. | MDC | Base | 143–145.5/EtOAc-ether | 88 |
| 2Q | Cl | 4-CH$_3$OC$_6$H$_4$ | — | (CH$_2$)$_2$ | Morph. | MDC | HCl | 170–173/EtOH | 58 |
| 2R | CH$_3$ | 4-C$_3$H$_7$C$_6$H$_4$ | — | (CH$_2$)$_2$ | Morph. | MDC | Base | 86.5–87.5/EtOAc-ether | 68 |
| 2S | CH$_3$ | 2-CH$_3$C$_6$H$_4$ | 5-F | (CH$_2$)$_3$ | Morph. | MDC | HCl | 215.5–219.5/EtOH | 76 |
| 2T | CH$_3$ | 4-FC$_6$H$_4$ | 5-F | (CH$_2$)$_3$ | Morph. | MDC | HCl | 223.0–225.0/EtOH | 43 |
| 2U | CH$_3$ | C$_6$H$_5$CH=CH$_2$ | 5-F | (CH$_2$)$_3$ | Morph. | MDC | HCl | 223.5–226.5/MeOH | 44 |
| 2V | CH$_3$ | 2,4-F$_2$C$_6$H$_3$ | 5-F | (CH$_2$)$_2$ | Morph. | MDC | Base | 118–120/i-PrOH | 24 |
| 2W | CH$_3$ | 2-FC$_6$H$_4$ | — | CHC$_2$H$_5$CH$_2$ | Morph. | MDC | Base | 162–165/EtOAc-hexane | 52 |
| 2X | CH$_3$ | 4-CH$_3$OC$_6$H$_4$ | — | CHC$_2$H$_5$CH$_2$ | Morph. | MDC | HCl | 153–157/i-PrOH-ether | 39 |
| 2Y | CH$_3$ | 1-naphthyl | — | CHCH$_3$CH$_2$ | Morph. | EDC | Maleate | 87/t-butyl methyl ether | 36 |
| 2Z | H | 1-naphthyl | — | (CH$_2$)$_2$ | Morph. | EDC | Base | 105–107/ether | 44 |
| 2AA | CH$_3$ | 5-benzo[b]furyl | — | (CH$_2$)$_2$ | Morph. | MDC | Base | 165.5–167/EtOAc-acetone | 46 |
| 2AB | CH$_3$ | 2,4-F$_2$C$_6$H$_3$ | — | (CH$_2$)$_2$ | Morph. | MDC | Base | 121–123.5/i-PrOH | 30 |
| 2AC | CH$_3$ | 2,4-F$_2$C$_6$H$_3$ | 5-F | (CH$_2$)$_3$ | Morph. | EDC | HCl | 212–216/EtOH | 33 |
| 2AD | CH$_3$ | 2-F-4-CH$_3$OC$_6$H$_3$ | — | (CH$_2$)$_2$ | Morph. | EDC | HCl | 258–260/EtOH | 25 |
| 2AE | CH$_3$ | 2-F-4-CH$_3$OC$_6$H$_3$ | 5-F | (CH$_2$)$_3$ | Morph. | EDC | HCl | 221–223.5/EtOH | 16 |
| 2AF | CH$_3$ | 4-BrC$_6$H$_4$ | 5-F | (CH$_2$)$_3$ | Morph. | MDC | HCl | 238–240/i-PrOH | 64 |
| 2AG | CH$_3$ | 2,6-F$_2$C$_6$H$_3$ | — | (CH$_2$)$_2$ | Morph. | EDC | Base | 117–119/EtOAc | 53 |
| 2AH | CH$_3$ | 2,3-(CH$_3$)$_2$C$_6$H$_3$ | — | (CH$_2$)$_2$ | Morph. | EDC | HCl.¼H$_2$O | 241–243/EtOH | 35 |
| 2AI | CH$_3$ | 3,5-Cl$_2$C$_6$H$_3$ | — | (CH$_2$)$_2$ | Morph. | MDC | Base | 145–146 | 55 |
| 2AJ | CH$_3$ | 3,5-(CH$_3$)$_2$C$_6$H$_3$ | — | (CH$_2$)$_2$ | Morph. | MDC | Base | 142–144/EtOH-hexane | 51 |
| 2AK | CH$_3$ | 3-CH$_3$C$_6$H$_4$ | — | (CH$_2$)$_2$ | Morph. | MDC | Base | 125–127 | 44 |
| 2AL | CH$_3$ | 3-ClC$_6$H$_4$ | — | (CH$_2$)$_2$ | Morph. | MDC | Base | 116–118/EtOAc-ether | 38 |
| 2AM | CH$_3$ | 3-FC$_6$H$_4$ | — | CHCH$_3$CH$_2$ | Morph. | EDC | Base | 85–87 | 27 |
| 2AN | CH$_3$ | 2-ClC$_6$H$_4$ | — | CHCH$_3$CH$_2$ | Morph. | EDC | HCl | 150(dec.)/EtOAc | 37 |
| 2AO | CH$_3$ | 1-naphthyl | 7-CH$_3$O | (CH$_2$)$_2$ | Morph. | EDC | Base | 225–227/EtOAc-ether | 11 |
| 2AP | CH$_3$ | 2-FC$_6$H$_4$ | 5-F | (CH$_2$)$_3$ | Morph. | MDC | HCl | 224–226/EtOH | 20 |
| 2AQ | CH$_3$ | 2-FC$_6$H$_4$ | 5-F | CHCH$_3$CH$_2$ | Morph. | MDC | HCl | 208–211/EtOAc | 49 |
| 2AR | CH$_3$ | 4-BrC$_6$H$_4$ | — | (CH$_2$)$_2$ | Morph. | EDC | HCl.¼H$_2$O | 257–260 | 13 |
| 2AS | CH$_3$ | 5-(1H-benzimidazolyl) | — | (CH$_2$)$_2$ | Morph. | MDC | Base | 173.5–175.5/EtOAc | 25 |
| 2AT | CH$_3$ | 4-Br-1-naphthyl | — | (CH$_2$)$_2$ | Morph. | MDC | Base | 126.5–128.5/EtOAc-ether | 35 |
| 2AU | H | 4-CH$_3$OC$_6$H$_4$ | — | CHCH$_3$CH$_2$ | Morph. | EDC | HCl.H$_2$O | 140 | 54 |
| 2AV | CH$_3$ | 2-naphthyl | — | CHC$_2$H$_5$CH$_2$ | Morph. | MDC | CH$_3$SO$_3$H | 214–216/i-PrOH | 32 |
| 2AW | H | 4-Br-1-naphthyl | — | (CH$_2$)$_2$ | Morph. | MDC | Base | 164–166/acetone | 43 |
| 2AX | H | 1-naphthyl | — | (CH$_2$)$_3$ | Morph. | MDC | Base | 143–144/EtOAc | 57 |
| 2AY | H | 1-naphthyl | 6-CH$_3$ | (CH$_2$)$_2$ | Morph. | MDC | Base | 163–165/EtOAc | 54 |
| 2AZ | CH$_3$ | 6-quinolyl | — | (CH$_2$)$_2$ | Morph. | MDC | Base | 138–139/EtOAc | 55 |
| 2BA | CH$_3$ | 7-quinolyl | — | (CH$_2$)$_2$ | Morph. | MDC | Base | 174–175 | 38 |
| 2BB | CH$_3$ | 8-quinolyl | — | (CH$_2$)$_2$ | Morph. | MDC | Base | 158–159/EtOAc | 28 |
| 2BC | CH$_3$ | 3-quinolyl | — | (CH$_2$)$_2$ | Morph. | MDC | Base | 165–166/MDC-MeOH | 34 |
| 2BD | CH$_3$ | 2-quinolyl | — | (CH$_2$)$_2$ | Morph. | MDC | Base | 163–164/MDC-MeOH | 51 |
| 2BE | CH$_3$ | 4-quinolyl | — | (CH$_2$)$_2$ | Morph. | MDC | Base | 142–143/EtOH | 63 |
| 2BF | H | 6-quinolyl | — | (CH$_2$)$_2$ | Morph. | MDC | Base | 123–124 | 37 |

TABLE 2-continued

| Example | $R_2$ | $R_3$ | $R_4$ | Alk | N=B | Solv. | Base/Salt | m.p./Solv. | Yield |
|---|---|---|---|---|---|---|---|---|---|
| 2BG | Cl | 1-naphthyl | — | $(CH_2)_2$ | Morph. | MDC | Base | 144-145/EtOAc | 48 |
| 2BH | $CH_3$ | 7-quinolyl | — | $(CH_2)_2$ | Morph. | MDC | Base | 125-126 | 41 |
| 2BI | $CH_3$ | 7-benzo[b]furyl | — | $(CH_2)_2$ | Morph. | MDC | Base | 161-162/EtOAc-hexane | 27 |
| 2BJ | H | 4-benzo[b]furyl | — | $(CH_2)_2$ | Morph. | MDC | Base | 160-162/EtOAc | 59 |
| 2BK | H | 6-benzo[b]furyl | — | $(CH_2)_2$ | Morph. | MDC | Base | 125-126 | 61 |
| 2BL | H | 7-benzo[b]furyl | — | $(CH_2)_2$ | Morph. | MDC | Base | 145-147/EtOAc | 80 |
| 2BM | $CH_3$ | benzyl | — | $(CH_2)_2$ | Morph. | MDC | HCl | 220-226/i-PrOH | 30 |
| 2BN | $CH_3$ | 4-$CH_3$O-styryl | — | $(CH_2)_2$ | Morph. | MDC | Base | 108.5-111/EtOH | 59 |
| 2BO | $CH_3$ | 2-(1-naphthyl)-ethenyl | — | $(CH_2)_2$ | Morph. | MDC | Base | 152-155.5/EtOAc | 40 |
| 2BP | H | 1-(tetra-H-naphthyl) | — | $(CH_2)_2$ | Morph. | MDC | HCl | 198-200 | 59 |
| 2BQ | H | 2-$FC_6H_4$ | — | $(CH_2)_2$ | Morph. | MDC | HCl | 210-212/i-PrOH | 14 |
| 2BR | H | 5-benzo[b]furyl | — | $(CH_2)_2$ | Morph. | MDC | Base | 158-159/EtOAc | 36 |
| 2BS | H | 4-$CH_3OC_6H_4$ | 6-F | $(CH_2)_3$ | Morph. | MDC | HCl | 201-203/MDC-ether | 37 |
| 2BT | H | $C_6H_5$ | 5-F | $(CH_2)_3$ | Morph. | MDC | Base | 102-103/Me-t-Bu-ether | 34 |
| 2BU | H | 3-$CH_3OC_6H_4$ | 5-F | $(CH_2)_3$ | Morph. | MDC | Maleate | 150-151/EtOH | 17 |
| 2BV | H | 4-$CH_3OC_6H_4$ | 5-F | $(CH_2)_2$ | Morph. | MDC | Base | 141-142/$CH_3CN$ | 80 |
| 2BW | $CH_3$ | 4-$CH_3OCH_2C_6H_4$ | — | $(CH_2)_2$ | Morph. | MDC | HCl.½$H_2O$ | 194-195/$CH_3CN$ | 13 |
| 2BX | H | 1-naphthyl | — | $CHCH_3CH_2$ | Morph. | EDC | Base | 115-118 | 26 |
| 2BY | H | 1-naphthyl | 5-Bzl.-O | $CH_2CH_2$ | Morph. | EDC | Base | 195-200/EtOAc | 24 |
| 2BZ | H | 3,4-$(CH_3O)_2C_6H_3$ | 5-HO(j) | $CH_2CH_2$ | Morph. | EDC | Base | 223-226/EtOAc | 6 |
| 2CA | $CH_3$ | 4-$CH_3$-1-naphthyl | — | $CH_2CH_2$ | Morph. | MDC | Base | 171-173 | 75 |
| 2CB | H | 4-$CH_3$-1-naphthyl | — | $CH_2CH_2$ | Morph. | MDC | Base | 158.5-160.5 | 76 |
| 2CC | H | 4-$CH_3OC_6H_4$ | 4-HO | $CH_2CH_2$ | Morph. | MDC | Base | 169-172/$CH_3CN$ | 18 |
| 2CD | H | 4-$CH_3OC_6H_4$ | 7-Bzl-O | $CH_2CH_2$ | Morph. | MDC | Base | oil | 36 |
| 2CE | H | 6-Cl-1-naphthyl | — | $CH_2CH_2$ | Morph. | MDC | Base | 173-173.5 | 60 |
| 2CF | $CH_3$ | 2,4-$Cl_2C_6H_3$ | — | $CH_2CH_2$ | Morph. | MDC | Base | 114-116 | 20 |
| 2CG | $CH_3$ | 2-pyrenyl | — | $CH_2CH_2$ | Morph. | MDC | Base | 157-159/EtOAc | 30 |
| 2CH | $CH_3$ | 2-$ClC_6H_5$ | — | $CH_2CH_2$ | Morph. | EDC | Base | 104-107 | 64 |
| 2CI | $CH_3$ | 2-$BrC_6H_5$ | — | $CH_2CH_2$ | Morph. | EDC | Base | 108-110/EtOAc-ether | 20 |
| 2CJ | H | 2-naphthyl | — | $(CH_2)_2$ | Morph. | MDC | Base | 170-172/EtOAc | 48 |

(i) The hydrochloride has m.p. 193-197 (from methanol-t-butyl methyl ether).
(j) Starting material was the corresponding 5-benzyloxy compound which was debenzylated during the reduction.

C. From the 2-$R_2$-$R_4$-Substituted-1-halo or 1-tosyloxy-1H-indoles

Example 3A

A solution of 20 g. (0.41 mole) of 2-methyl-3-(1-naphthylcarbonyl)-1-[2-(p-toluenesulfonyloxy)ethyl]-1H-indole (Preparation 4A) and 8.5 g. (0.1 mole) of piperidine in 50 ml. of dry DMF was heated under reflux for about twenty-four hours, and the mixture was then diluted with ethyl acetate and washed with water. The organic layer was dried over magnesium sulfate, filtered and concentrated to dryness to give the product, in the form of the free base, as a brown oil which was dissolved in ethyl acetate and chromatographed on silica gel, the product being eluted with 1:1 ethyl acetate:hexane. There was thus obtained 5.2 g. (32%) of 2-methyl-3-(1-naphthylcarbonyl)-1-[2-(1-piperidinyl)ethyl]-1H-indole, m.p. 119°-121° C.

Following a procedure similar to that described in Example 3A above, the following 2-$R_2$-$R_4$-substituted-3-$R_3$-carbonyl-1-amino-lower-alkyl-1H-indoles in Table 3 below were prepared by reaction of a 2-methyl-3-$R_3$-carbonyl-1-(2-tosyloxyethyl)-1H-indole or a 2-methyl-3-$R_3$-carbonyl-1-(halo-lower-alkyl)-1H-indole with an appropriate amine, $HN=B$, where $R_2$, in each instance, is $CH_3$. The starting material in each of Examples 3B-3F and 3K was the corresponding 1-(2-tosyloxyethyl)-1H-indole; in Example 3G the corresponding 1-(3-chloro-propyl)-1H-indole; and in each of Examples 3H, 3I and 3J the corresponding 1-(bromo-lower-alkyl)-1H-indole.

TABLE 3

| Example | $R_3$ | $R_4$ | Alk | N=B | Solv. | Base/Salt | m.p./Solv. | Yield |
|---|---|---|---|---|---|---|---|---|
| 3B | 4-$CH_3OC_6H_4$ | — | $(CH_2)_2$ | 3-HO-1-piperidinyl | $CH_3CN$ | HCl.½$H_2O$(k) | 160 | 31 |
| 3C | 4-$C_2H_5C_6H_4$ | — | $(CH_2)_2$ | 3-HO-1-piperidinyl | $CH_3CN$ | Base | 139-141 | 57 |
| 3D | 1-naphthyl | — | $(CH_2)_2$ | 3-HO-1-piperidinyl | DMF | HCl.$H_2O$. 1/6i-PrOH | 175-180/i-PrOH-ether | 24 |
| 3E | 1-naphthyl | — | $(CH_2)_2$ | 2-$CH_3$-4-morpholinyl | DMF | Base | 144-145/ether | 21 |
| 3F | 4-$CH_3OC_6H_4$ | — | $(CH_2)_2$ | 2-$CH_3$-4-morpholinyl | DMF | maleate.½EtOAc | 135-140/EtOAc | 52 |
| 3G | 4-$CH_3OC_6H_4$ | 5-F | $(CH_2)_3$ | 3-HO-1-piperidinyl | DMF | HCl | 126-128/MeOH-ether | 69 |
| 3H | 4-$CH_3OC_6H_4$ | 5-F | $(CH_2)_3$ | 2-$CH_3$-4-morpholinyl | DMF | HCl | 216-217/i-PrOH | 85 |
| 3I | 4-$CH_3OC_6H_4$ | — | $(CH_2)_3$ | 1-piperidinyl | DMF | HCl | 201-203/i-PrOH-ether | 80 |
| 3J | 4-$CH_3OC_6H_4$ | — | $(CH_2)_3$ | $N(C_2H_5)_2$ | DMF | HCl | 179-181/$CH_3CN$ | 11 |
| 3K | 1-naphthyl | — | $(CH_2)_2$ | 3-$CH_3$-4-morpholinyl | DMF | HCl | 149-154 | 5 |

(k) The anhydrous hydrochloride has m.p. 224-226 (from ethanol).

D. Miscellaneous Processes

Example 4A

2-Methyl-3-(3-nitrobenzoyl)-1-[2-(4-morpholinyl)-ethyl]-1H-indole (8.0 g., 0.02 mole) dissolved in 175 ml. of ethyl acetate and 75 ml. of acetic acid was reduced with hydrogen in a Parr shaker over 0.3 g. of platinum oxide. The product was isolated in the form of the free base and recrystallized from ethyl acetate to give 6.0 g. (83%) of 2-methyl-3-(3-aminobenzoyl)-1-[2-(4-morpholinyl)ethyl]-1H-indole, m.p. 167°-169° C.

Example 4B

Following a procedure similar to that described in Example 4A above, 28 g. (0.07 mole) of 2-methyl-3-(4-nitrobenzoyl)-1-[2-(4-morpholinyl)ethyl]-1H-indole in 100 ml. of glacial acetic acid and 100 ml. of ethyl acetate was reduced with hydrogen over platinum oxide and the product, in the form of the free base, was recrystallized from ethyl acetate to give 19.05 g. (75%) of 2-methyl-3-(4-aminobenzoyl)-1-[2-(4-morpholinyl)ethyl]-1-H-indole, m.p. 154°–156° C.

A small amount of the free base was reacted with methanesulfonic acid and the product recrystallized from ethanol to give the corresponding methanesulfonate as an orange powder, m.p. 221°–223° C.

Example 5A

A mixture of 5 g. (0.012 mole) of 2-methyl-3-(2,3-dimethoxybenzoyl)-1-[2-(4-morpholinyl)ethyl]-1H-indole and 7.1 g. (0.061 mole) of pyridine hydrochloride was heated under reflux under a nitrogen atmosphere for three hours, allowed to stand at ambient temperature for about forty-eight hours and then poured into an ice/water mixture and extracted with MDC. The combined organic extracts were washed with sodium carbonate, then with water, dried and taken to dryness to give 1.8 g. (39%) of 2-methyl-3-(2,3-dihydroxybenzoyl)-1-[2-(4-morpholinyl)ethyl]-1H-indole, m.p. 119°–121° C.

Example 5B

To a solution of 5.17 g. (0.01 mole) of 5-benzyloxy-3-(1-naphthylcarbonyl)-1-[2-(4-morpholinyl)ethyl]-1H-indole in 225 ml. of absolute ethanol was added 1 g. of 10% palladium-on-charcoal catalyst, and the mixture was reduced with hydrogen at ambient temperature and 55 p.s.i.g hydrogen pressure. When reduction was complete, the catalyst was removed by filtration, the filtrate taken to dryness and the residue partitioned between chloroform and aqueous sodium bicarbonate. The organic layer was separated, dried and taken to dryness to give 2.4 g. (60%) of 5-hydroxy-3-(1-naphthylcarbonyl)-1-[2-(4-morpholinyl)ethyl]-1H-indole, m.p. 200°–202° C.

Example 5C

To a solution of 2.0 g. (0.0043 mole) of 7-benzyloxy-3-(4-methoxybenzoyl)-1-[2-(4-morpholinyl)ethyl]-1H-indole in 25 ml. of ethanol was added two small scoops of 10% palladium-on-charcoal catalyst, and the mixture was heated under reflux and then treated cautiously with 2.02 g. (0.032 mole) of ammonium formate. The mixture was heated under reflux for about one half hour, cooled, diluted with water and extracted with MDC. The combined organic extracts were dried, taken to dryness and the residue recrystallized from acetonitrile to give 1.6 g. (97%) of 7-hydroxy-3-(4-methoxybenzoyl)-1-[2-(4-morpholinyl)ethyl]-1H-indole, m.p. 203°–205° C.

Example 6

A solution of 15 g. (0.04 mole) of 2-methyl-3-(4-aminobenzoyl)-1-[2-(4-morpholinyl)ethyl]-1H-indole, 12 g. (0.4 mole) of formaldehyde and 7.5 g. (0.119 mole) of sodium cyanoborohydride in 250 ml. of acetonitrile was stirred for thirty minutes and then treated dropwise with acetic acid until acidic. The mixture was stirred for about eighteen hours, then poured into aqueous potassium hydroxide and the mixture extracted with ether. The organic extracts, on drying over magnesium sulfate and concentration to dryness, afforded a yellow solid which was recrystallized from isopropanol to give 7.5 g. (48%) of 3-(4-dimethylaminobenzoyl)-2-methyl-1-[2-(4-morpholinyl)ethyl]-1H-indole, m.p. 152°–154° C.

Example 7A

A mixture of 9.54 g. (0.02 mole) of 3-(4-bromo-1-naphthylcarbonyl)-2-methyl-1-[2-(4-morpholinyl)ethyl]-1H-indole and 4.4 g. (0.48 mole) of cuprous cyanide in 50 ml. of DMF containing 5 drops of pyridine was heated under reflux for eight hours and the mixture then poured into 10% ammonium hydroxide. The solid which separated was collected by filtration, dissolved in MDC and the solution passed through a column of silica gel. The eluate was diluted with ethyl acetate, and the solid which separated on standing was collected and dried to give 4.8 g. (56%) of 2-methyl-3-(4-cyano-1-naphthylcarbonyl)-1-[2-(4-morpholinyl)ethyl]-1H-indole, m.p. 180.5°–183.5° C.

Examples 7B–7D

Following a procedure similar to that described in Example 7A above, reaction of a 2-R$_2$-3-(4-bromo-1-naphthylcarbonyl)-1-[2-(4-morpholinyl)ethyl]-1H-indole either with a molar equivalent of cuprous cyanide in DMF in the presence of a small amount of pyridine (to prepare the corresponding 4-cyano-1-naphthylcarbonyl compound) or with molar equivalent amounts of cuprous bromide and imidazole in DMF in the presence of a molar excess of potassium carbonate (to prepare the corresponding 1-[4-(1-imidazolyl)]naphthylcarbonyl compounds) afforded the species of formula I in Table 5 where, in each instance, R$_4$ is H; Alk is CH$_2$CH$_2$; and N=B is 4-morpholinyl. All products were isolated in the form of the free bases.

TABLE 4

| Example | R$_3$ | R$_2$ | m.p./Solv. | Yield |
|---|---|---|---|---|
| 7B | 1-[4-(1-imidazolyl)naphthyl] | CH$_3$ | 173.5–177/EtOAc | 5 |
| 7C | 1-[4-(1-imidazolyl)naphthyl] | H | 198–200/EtOAc | 78 |
| 7D | 4-cyano-1-naphthyl | H | 186.5–189.0/EtOAc | 77 |

A solution of 4 g. (0.01 mole) of 2-chloro-3-(4-methoxybenzoyl)-1-[2-(4-morpholinyl)ethyl]-1H-indole and 10 g. of potassium fluoride in 100 ml. of DMF was heated under reflux for about twenty hours and then poured into an ice/water mixture and extracted with ethyl acetate. The combined organic extracts were washed with water, then with brine, dried and taken to dryness and the residue recrystallized from ethanol to give 1.7 g. of 2-fluoro-3-(4-methoxybenzoyl)-1-[2-(4-morpholinyl)ethyl]-1H-indole, m.p. 134°–135° C.

Example 9

A solution of 18 g. (0.05 mole) of 2-methyl-3-(4-methoxybenzoyl)-1-[2-(4-morpholinyl)ethyl]-1H-indole, 6 g. (0.042 mole) of phosphorus pentasulfide in 100 ml. of pyridine was heated on a steam bath for one hour, then cooled and poured into 300 ml. of water, and an aqueous solution containing 11.5 g. (0.108 mole) of sodium carbonate was added with stirring. Extraction of the mixture with ethyl acetate and drying and evaporation of the extracts to dryness afforded 18 g. (91%) of 2-methyl-3-(4-methoxyphenylthiocarbonyl)-1-[2-(4-morpholinyl)-ethyl]-1H-indole, m.p. 138°–139° C.

Example 10

To a solution of 20 g. (0.055 mole) of 2-methyl-3-(4-aminobenzoyl)-1-[2-(4-morpholinyl)ethyl]-1H-indole (Example 4B) in 200 ml. of MDC was added 14.4 g. (0.068 mole) of trifluoroacetic anhydride, the solution was allowed to stand at ambient temperature for fifteen minutes and then taken to dryness in vacuo. Recrystallization of the solid residue from pentane gave 22 g. (92%) of 2-methyl-3-(4-trifluoroacetylaminobenzoyl)-1-[2-(4-morpholinyl)ethyl]-1H-indole.

A mixture of the latter (0.049 mole), 35.9 g. (0.19 mole) of iodobutane and 48 g. (0.343 mole) of potassium carbonate in 250 ml. of acetone was heated under reflux until no unreacted starting material could be detected by thin layer chromatography and then taken to dryness in vacuo. The mixture was partitioned between water and MDC, the aqueous layer extracted with additional MDC and the combined organic extracts washed with brine, dried and taken to dryness in vacuo. The residue was dissolved in diethyl ether, the solution treated with excess ethereal hydrogen chloride, and the solid which separated was collected and dried to give 24 g. (95%) of 2-methyl-3-[4-(N-butyl-N-trifluoroacetylamino)benzoyl]-1-[2-(4-morpholinyl)ethyl]-1H-indole.

The latter (0.047 mole) was dissolved in 100 ml. of ethanol and 500 ml. of 10% sodium hydroxide, the solution was heated under reflux for two hours, taken to dryness in vacuo, and the residue chromatographed on silica gel, eluting with 25% acetone/hexane. The higher $R_f$ fraction was collected and recrystallized from ethyl acetate to give 2.6 g. (13%) of 2-methyl-3-(4-butylaminobenzoyl)-1-[2-(4-morpholinyl)ethyl]-1H-indole, m.p. 129.0°–130.0° C.

BIOLOGICAL TEST RESULTS

Data obtained in the mouse vas deferens test (MVD) and in the CP55490 binding assay (CP), expressed as the $IC_{50}$ in $\mu M$, for the compounds described above, identified by the example number where their preparations are described, are given in Table 5 below. Compounds are considered active in the MVD test at $IC_{50}$ levels of 5.0 $\mu M$ or less.

TABLE 5

| Example | MVD | CP |
|---|---|---|
| 1A | 0.1 | 59% I/1µM |
| 1B | 0.5 | 3–10 |
| 1C | 0.61 | |
| 1D | 0.178 | |
| 1E | 0.12 | |
| 1F | 1.4 | |
| 1H | 0.36 | |
| 1J | 0.073 | |
| 1K | 0.26 | |
| 1L | 0.54 | |
| 1M | 0.28 | |
| 1-O | 1.3 | |
| 1P | 0.32 | |
| 1Q | 0.018 | ≈50 |
| 1R | 0.09 | |
| 1S | 0.05 | |
| 1U | 1.9 | |

TABLE 5-continued

| Example | MVD | CP |
|---|---|---|
| 1X | 0.071 | |
| 1Z | 0.44 | |
| 1AA | 0.2 | |
| 1AB | 0.068 | |
| 1AE | 0.7 | |
| 1AF | 1.1 | |
| 1AG | 0.56 | |
| 1AK | 0.9 | |
| 1AP | 0.015 | 51.0 |
| 1AV | 0.026 | |
| 1AW | 0.46 | |
| 1AX | >10 | |
| 1BJ | 0.31 | |
| 1BO | 1.6 | |
| 1BP | 0.26 | |
| 1BQ | 0.42 | |
| 1BU | 0.111 | |
| 1BV | 0.015 | |
| 1BW | 0.02 | |
| 1BX | 0.06 | |
| 1BZ | 4.3 | |
| 1CA | 0.07 | 70% I/1µM |
| 1CB | 0.09 | |
| 1CD | 0.04 | |
| 1CE | 0.007 | |
| 1CF | 0.06 | |
| 1CG | 0.17 | |
| 1CH | 1.6 | |
| 1CI | 0.24 | |
| 1CJ | >10 | |
| 2C | 0.49 | |
| 2E | 2.4 | |
| 2G | 1.3 | |
| 2H | 0.177 | |
| 2K | 0.71 | |
| 2N | 0.052 | |
| 2Q | 0.176 | |
| 2Y | 0.01 | |
| 2Z | 0.006 | 88.0 |
| 2AA | 0.125 | |
| 2AD | 0.18 | |
| 2AG | 0.37 | |
| 2AJ | 0.39 | |
| 2AM | 0.86 | |
| 2AR | 0.62 | |
| 2AT | 0.034 | |
| 2AU | 3.7 | |
| 2AV | 0.091 | |
| 2AW | 0.005 | |
| 2AX | 0.01 | |
| 2AY | 0.002 | |
| 2AZ | 0.102 | |
| 2BA | 0.093 | |
| 2BB | 0.129 | |
| 2BC | 0.57 | |
| 2BD | 0.099 | |
| 2BE | 0.115 | |
| 2BF | 0.142 | |
| 2BG | 0.006 | |
| 2BH | 0.088 | |
| 2BI | 0.017 | |
| 2BJ | 0.007 | |
| 2BK | 0.040 | |
| 2BL | 0.004 | |
| 2BM | 0.174 | |
| 2BN | 0.138 | |
| 2BO | 0.13 | |
| 2BP | 0.01 | |
| 2BQ | 0.5 | |
| 2BR | 0.03 | |
| 2BW | 0.9 | |
| 1BZ | 0.2 | |
| 2CA | 0.009 | |
| 2CB | 0.003 | |
| 2CE | 0.088 | |
| 2CF | 0.2 | |
| 2CG | 0.04 | |
| 2CH | 0.091 | |
| 2CJ | 0.031 | |
| 3A | 0.066 | |
| 3B | >10 | |

TABLE 5-continued

| Example | MVD | CP |
| --- | --- | --- |
| 3D | 0.236 | 200–500 |
| 3E | 0.21 | |
| 3J | >10 | |
| 3K | 0.03 | |
| 4A | 0.7 | |
| 4B | 0.52 | |
| 5A | 0.18 | |
| 5B | 0.02 | |
| 5C | 0.4 | |
| 7A | 0.014 | |
| 7B | 0.005 | |
| 7C | 0.008 | |
| 7D | 0.005 | |
| 9 | 0.11 | |

We claim:

1. A member of the group consisting of (A) compounds having the formula:

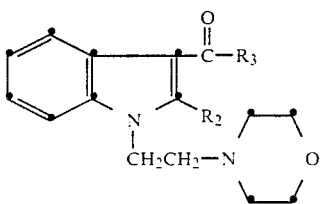

wherein:
$R_2$ is hydrogen or lower-alkyl; and
$R_3$ is lower-alkoxymethylphenyl, benzyl, lower-alkoxystyryl, (1H-imidazol-1-yl)-naphthyl, 2-(1-naphthyl)ethenyl, 1-(1,2,3,4-tetrahydronaphthyl), anthryl, phenanthryl or pyrenyl; and (B) acid-addition salts thereof.

2. A compound according to claim 1 wherein $R_2$ is hydrogen.

3. A compound according to claim 1 wherein $R_2$ is lower-alkyl.

4. 3-[1-(1,2,3,4-Tetrahydronaphthyl)carbonyl]-1-[2-(4-morpholinyl)ethyl]-1H-indole or an acid-addition salt thereof according to claim 2.

5. 3-Benzylcarbonyl-2-methyl-1-[2-(4-morpholinyl)ethyl]-1H-indole or an acid-addition salt thereof according to claim 3.

6. 3-(4-Methoxycinnamoyl)-2-methyl-1-[2-(4-morpholinyl)ethyl]-1H-indole or an acid-addition salt thereof according to claim 3.

7. 3-(4-Methoxymethylbenzoyl)-2-methyl-1-[2-(4-morpholinyl)ethyl]-1H-indole or an acid-addition salt thereof according to claim 3.

8. 3-(1-Anthrylcarbonyl)-2-methyl-1-[2-(4-morpholinyl)ethyl]-1H-indole or an acid-addition salt thereof according to claim 3.

9. 3-(9-Phenanthrylcarbonyl)-2-methyl-1-[2-(4-morpholinyl)ethyl]-1H-indole or an acid-addition salt thereof according to claim 3.

10. 3-(1-Pyrenylcarbonyl)-2-methyl-1-[2-(4-morpholinyl)ethyl]-1H-indole or an acid-addition salt thereof according to claim 3.

11. 3-[2-(1-Naphthyl)ethenylcarbonyl]-2-methyl-1-[2-(4-morpholinyl)ethyl]-1H-indole or an acid-addition salt thereof according to claim 3.

* * * * *

UNITED STATES PATENT AND TRADEMARK OFFICE
CERTIFICATE OF CORRECTION

PATENT NO. : 5,013,837
DATED : May 7, 1991
INVENTOR(S) : Susan J. Ward & Malcolm R. Bell It is certified that error appears in the above-identified patent and that said Letters Patent is hereby corrected as shown below:

Column 15, line 1S and Column $R_2$ of table 1 "H"
should read --$CH_3$--.

Column 15 line 1T and column $R_2$ of table 1 "$CH_3$"
should read --H--.

Column 21 between lines 63 and 64 insert -- Examples 3B-3K--.

Column 24 after table 4 and before line 54 insert
--Example 8 --.

Signed and Sealed this

Twenty-ninth Day of September, 1992

Attest:

DOUGLAS B. COMER

*Attesting Officer*    *Acting Commissioner of Patents and Trademarks*